United States Patent
Le Flohic et al.

(10) Patent No.: US 8,835,627 B2
(45) Date of Patent: Sep. 16, 2014

(54) PROCESS FOR THE SYNTHESIS OF IVABRADINE AND ADDITION SALTS THEREOF WITH A PHARMACEUTICALLY ACCEPTABLE ACID

(71) Applicant: Les Laboratoires Servier, Suresnes Cedex (FR)

(72) Inventors: Alexandre Le Flohic, Fauville en Caux (FR); Mathieu Grandjean, La Frenaye (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/849,798

(22) Filed: Mar. 25, 2013

(65) Prior Publication Data

US 2013/0261298 A1    Oct. 3, 2013

(30) Foreign Application Priority Data

Mar. 27, 2012 (FR) ..................................... 12 52728

(51) Int. Cl.
| | | |
|---|---|---|
| *C07C 253/30* | (2006.01) | |
| *C07C 227/18* | (2006.01) | |
| *C07C 255/43* | (2006.01) | |
| *C07C 229/34* | (2006.01) | |
| *C07C 55/07* | (2006.01) | |
| *C07D 223/16* | (2006.01) | |
| *C07C 217/58* | (2006.01) | |

(52) U.S. Cl.
CPC ............ *C07D 223/16* (2013.01); *C07C 255/43* (2013.01); *C07C 253/30* (2013.01); *C07C 229/34* (2013.01); *C07C 2102/22* (2013.01); *C07C 55/07* (2013.01); *C07B 2200/07* (2013.01); *C07C 227/18* (2013.01); *C07C 217/58* (2013.01)

USPC ........................ 540/523; 558/408; 562/561

(58) Field of Classification Search
USPC ............ 540/523; 558/408; 562/561; 564/387
See application file for complete search history.

(56) References Cited

U.S. PATENT DOCUMENTS 8,278,440 B2    10/2012 Peglion et al.

FOREIGN PATENT DOCUMENTS

| EP | 2364972 | | 9/2011 |
| FR | 2364972 A1 | * | 9/2011 |
| IN | WO2008/065681 | * | 6/2008 |
| WO | WO 2008/065681 | | 6/2008 |
| WO | WO 2011/033194 | | 3/2011 |

OTHER PUBLICATIONS

"Ivabradine Hydrochloride Antianginal HCN (LF Current) Blocker" Drugs of the Future, vol. 27, No. 7, p. 652-658, 2003.
French Preliminary Search Report for FR 1252728 of Nov. 12, 2012.

* cited by examiner

*Primary Examiner* — Kristin Vajda
*Assistant Examiner* — Valerie Rodriguez-Garcia
(74) *Attorney, Agent, or Firm* — Hueschen and Sage

(57) ABSTRACT

Process for the synthesis of ivabradine of formula (I):

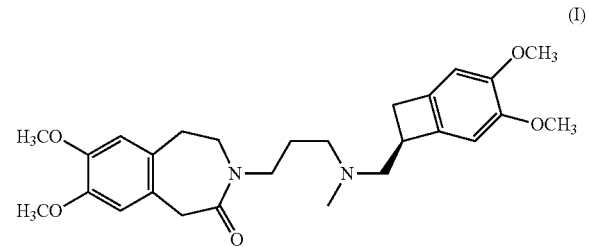

and addition salts thereof with a pharmaceutically acceptable acid.

35 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

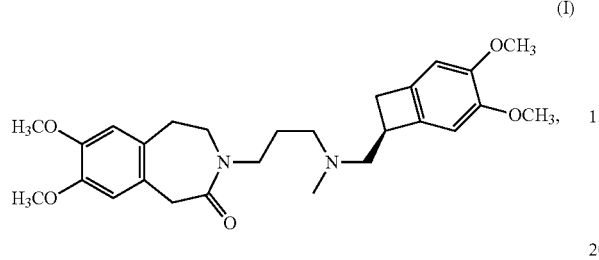

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, addition salts thereof with a pharmaceutically acceptable acid, and hydrates thereof.

Ivabradine, and its addition salts with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the synthesis of ivabradine hydrochloride starting from the compound of formula (II):

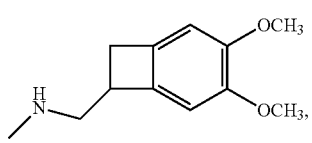

which is resolved to yield the compound of formula (III):

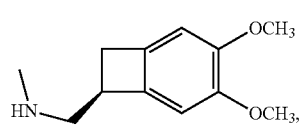

which is reacted with the compound of formula (IV):

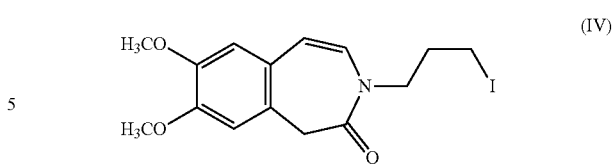

to yield the compound of formula (V):

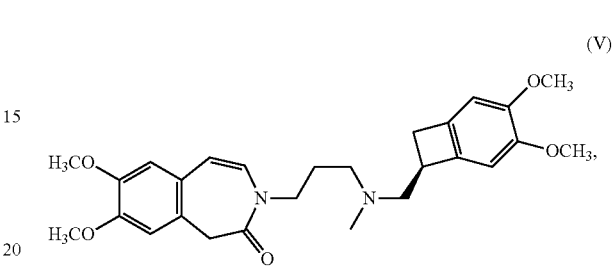

the catalytic hydrogenation of which yields ivabradine, which is then converted into its hydrochloride.

The disadvantage of that synthesis route is that it results in ivabradine in a yield of only 1%.

In view of the pharmaceutical value of this compound, it has been important to be able to obtain it by an effective synthesis process resulting in ivabradine in a good yield.

The present invention relates to a process for the synthesis of ivabradine of formula (I):

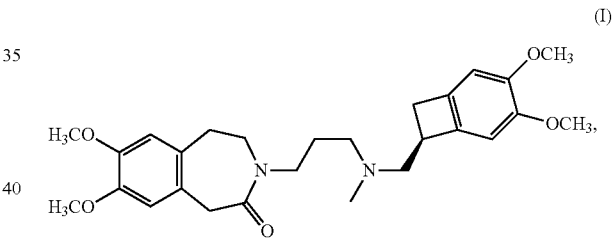

which process is characterised in that the compound of formula (VI):

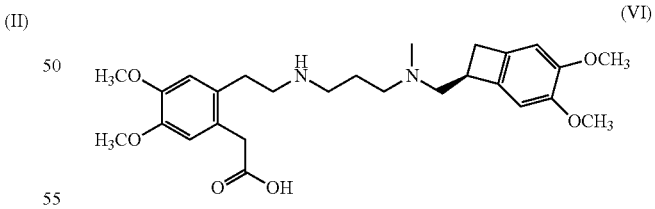

is subjected to a lactamisation reaction,
in the presence of a coupling agent and a base,
in an organic solvent,
to yield ivabradine of formula (I), which may be converted into addition salts thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

Among the coupling agents that may be used for the reaction for lactamisation of the compound of formula (VI) there may be mentioned, without implying any limitation, the following reagents: oxalyl chloride, thionyl chloride, N,N-dicyclohexylcarbodiimide (DCC), 1-ethyl-3-(3-dimethylaminopropyl)carbodiimide (EDCI), N,N-carbonyldiimidazole (CDI), 1-propanephosphonic acid cyclic anhydride (T3P) and 1-(methylsulphonyl)-1H-benzotriazole. The coupling agent preferably used for the reaction for lactamisation of the compound of formula (VI) is thionyl chloride.

The amount of thionyl chloride preferably used for carrying out the reaction for lactamisation of the compound of formula (VI) is between 1 and 5 equivalents, inclusive.

Among the bases that may be used for carrying out the reaction for lactamisation of the compound of formula (VI) there may be mentioned, without implying any limitation, triethylamine, diisopropylethylamine and pyridine.

The base preferably used for carrying out the reaction for lactamisation of the compound of formula (VI) is triethylamine.

Among the organic solvents that may be used for carrying out the reaction for lactamisation of the compound of formula (VI) there may be mentioned, without implying any limitation, dichloromethane, tetrahydrofuran, acetonitrile, acetone and toluene.

The organic solvent preferably used for carrying out the reaction for lactamisation of the compound of formula (VI) is dichloromethane.

The reaction for lactamisation of the compound of formula (VI) is preferably carried out at a temperature between 0° C. and 40° C., inclusive.

The present invention likewise relates to a process for the synthesis of ivabradine starting from the compound of formula (VI), which process is characterised in that said compound of formula (VI) is prepared starting from the compound of formula (VII):

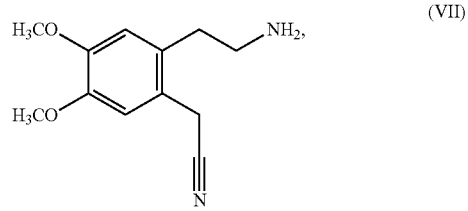 [SMILES: COc1cc(CC#N)c(CCN)cc1OC]

(VII)

which is reacted with the compound of formula (VIII):

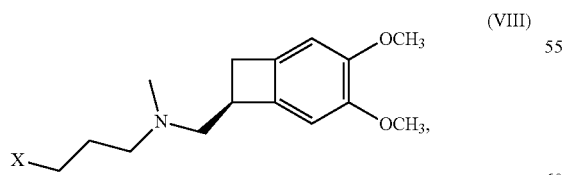

(VIII)

wherein X represents a halogen atom, a mesylate group or a tosylate group, in the presence of a base, in an organic solvent, to yield the compound of formula (IX):

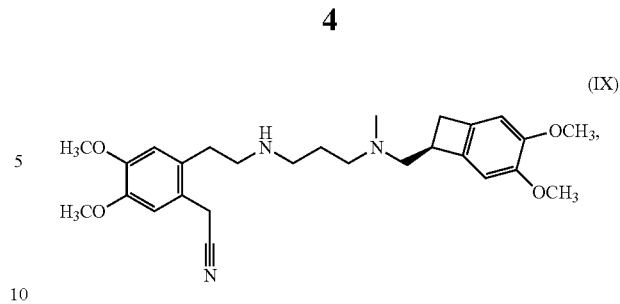

(IX)

which is hydrolysed, by the action of a base in a mixture of organic solvent and water, to form the compound of formula (VI):

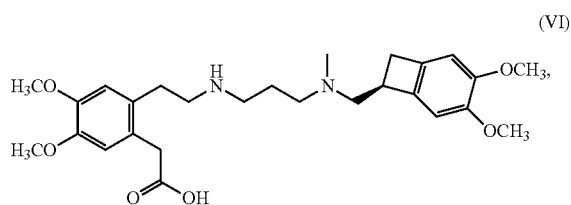 [SMILES: COc1cc(CCNCCCN(C)C[C@H]2Cc3cc(OC)c(OC)cc32)c(CC(=O)O)cc1OC]

(VI)

which is converted into ivabradine of formula (I):

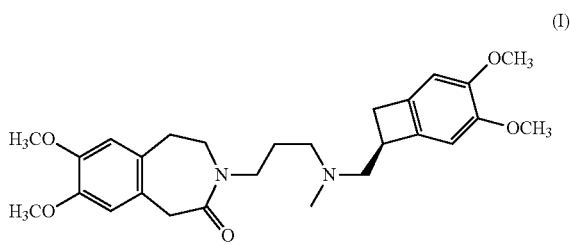 [SMILES: COc1cc2c(cc1OC)CC(=O)N(CCCN(C)C[C@H]1Cc3cc(OC)c(OC)cc31)CC2]

(I)

in accordance with the process described hereinbefore.

The present invention likewise relates to a process for the synthesis of ivabradine starting from the compound of formula (VI), which process is characterised in that said compound of formula (VI) is prepared starting from the compound of formula (X):

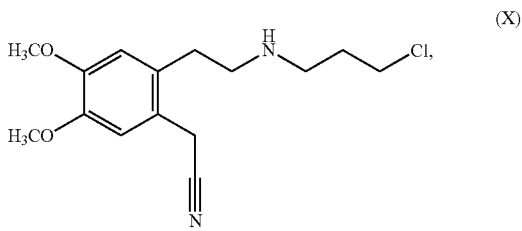 [SMILES: COc1cc(CC#N)c(CCNCCCCl)cc1OC]

(X)

which is reacted with the hydrochloride of the compound of formula (III):

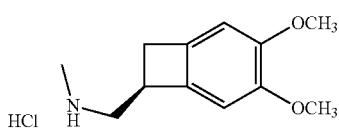

in the presence of a base, in an organic solvent,
to yield the compound of formula (IX):

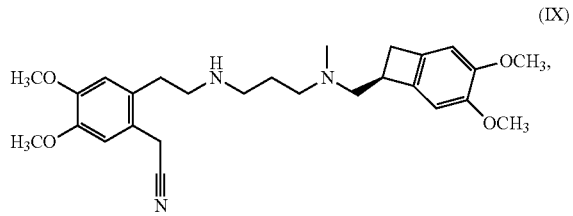 [SMILES: COc1cc(CC#N)c(CCNCCCN(C)C[C@H]2Cc3cc(OC)c(OC)cc32)cc1OC]

which is hydrolysed, by the action of a base in a mixture of organic solvent and water, to form the compound of formula (VI):

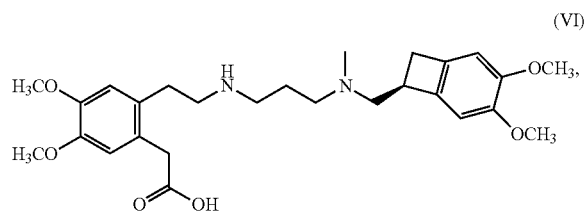 [SMILES: COc1cc(CCNCCCN(C)C[C@H]2Cc3cc(OC)c(OC)cc32)c(CC(=O)O)cc1OC]

which is converted into ivabradine of formula (I):

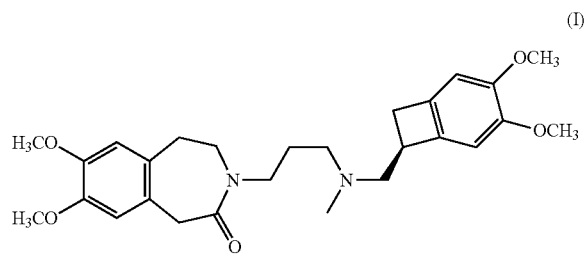 [SMILES: COc1cc2c(cc1OC)CC(=O)N(CCCN(C)C[C@H]1Cc3cc(OC)c(OC)cc31)CC2]

in accordance with the process described hereinbefore.

Among the bases that may be used to carry out the alkylation reaction between the compound of formula (VII) and the compound of formula (VIII) or the alkylation reaction between the compound of formula (X) and the hydrochloride of the compound of formula (III) there may be mentioned, without implying any limitation, inorganic bases, such as potassium carbonate, sodium carbonate, caesium carbonate, potassium hydrogen carbonate and sodium hydrogen carbonate, and organic bases, such as triethylamine, diisopropylethylamine and pyridine.

The base preferably used to carry out the alkylation reaction between the compound of formula (VII) and the compound of formula (VIII) or the alkylation reaction between the compound of formula (X) and the hydrochloride of the compound of formula (III) is triethylamine.

Among the organic solvents that may be used to carry out the alkylation reaction between the compound of formula (VII) and the compound of formula (VIII) or the alkylation reaction between the compound of formula (X) and the hydrochloride of the compound of formula (III) there may be mentioned, without implying any limitation, acetonitrile, acetone, methyl ethyl ketone (MEK), dimethylformamide (DMF), N-methylpyrrolidone (NMP) and dimethyl sulphoxide (DMSO).

The organic solvent preferably used to carry out the alkylation reaction between the compound of formula (VII) and the compound of formula (VIII) or the alkylation reaction between the compound of formula (X) and the hydrochloride of the compound of formula (III) is acetonitrile.

The alkylation reaction between the compound of formula (VII) and the compound of formula (VIII) or the alkylation reaction between the compound of formula (X) and the hydrochloride of the compound of formula (III) is preferably carried out at a temperature between 20° C. and 100° C., inclusive.

Among the bases that may be used to carry out the hydrolysis of the compound of formula (IX) to form the compound of formula (VI) there may be mentioned, without implying any limitation, potassium hydroxide, sodium hydroxide, lithium hydroxide and barium hydroxide.

The base preferably used to carry out the hydrolysis of the compound of formula (IX) to form the compound of formula (VI) is sodium hydroxide.

The organic solvent preferably used to carry out the hydrolysis of the compound of formula (IX) to form the compound of formula (VI) is an alcoholic solvent.

Among the alcoholic solvents that may be used to carry out the hydrolysis of the compound of formula (IX) to form the compound of formula (VI) there may be mentioned, without implying any limitation, methanol, ethanol, isopropanol and butanol.

The alcoholic solvent preferably used to carry out the hydrolysis of the compound of formula (IX) to form the compound of formula (VI) is ethanol.

The hydrolysis of the compound of formula (IX) to form the compound of formula (VI) is preferably carried out at a temperature between 0° C. and 110° C., inclusive.

The compounds of formulae (VI), (IX) and (X) and also 3-[{[(7S)-3,4-dimethoxybicyclo[4.2.0]octa-1,3,5-trien-7-yl]methyl}(methyl)amino]-1-propanol, ethyl N-{2-[2-(cyanomethyl)-4,5-dimethoxyphényl]ethyl}-β-alaninate oxalate and (2-{2-[(3-hydroxypropyl)amino]ethyl}-4,5-dimethoxyphenyl)acetonitrile are new compounds, for use as synthesis intermediates in the chemical or pharmaceutical industry, especially in the synthesis of ivabradine, addition salts thereof with a pharmaceutically acceptable acid and hydrates thereof, and as such form an integral part of the present invention.

LIST OF ABBREVIATIONS USED

DMF: dimethylformamide
DMSO: dimethyl sulphoxide
NMR: Nuclear Magnetic Resonance
m.p.: melting point
THF: tetrahydrofuran The NMR spectra are recorded on a Bruker apparatus at 400 MHz for the proton spectra and at 100 MHz for the carbon spectra.

The chemical shifts are expressed in terms of ppm (internal standard: TMS).

The following abbreviations are used to describe the peaks: singlet (s), doublet (d), doublet of doublets (dd), triplet (t), quadruplet (q), multiplet (m).

The Examples hereinbelow illustrate the invention.

Preparation A:

N-[2-(3,4-dimethoxyphenyl)ethyl]-2,2,2-trifluoroacetamide

To a solution of 2-(3,4-dimethoxyphenyl)ethanamine (50 g, 276 mmoles) in 350 mL of ethyl acetate stirred at ambient temperature there is added, dropwise, a solution of trifluoroacetic anhydride (46.1 mL, 330 mmoles) in 40 mL of ethyl acetate. After being in contact for 1 hour at ambient temperature, the mixture is hydrolysed using 100 mL of water. The organic phase is washed with a mixture of water/triethylamine (100 mL/38.5 mL), and 100 mL of saturated aqueous NaCl solution and is then dried over $MgSO_4$ and subjected to drying to obtain 65.8 g of a beige solid corresponding to the title compound.

Yield: 86%
m.p.: 93° C.
$^1$H NMR ($CDCl_3$, 400 MHz): 2.86 ppm (2H, t)—3.62 ppm (2H, q)—3.89 ppm (6H, s)—6.52 ppm (NH)—6.71 ppm and 6.84 ppm (3H, m).
$^{13}$C NMR ($CDCl_3$, 100 MHz): 34.4 ppm ($CH_2$)—41.3 ppm ($CH_2$)—55.8 ppm ($2CH_3$)—111.6 ppm and 111.8 ppm (2CH)—115.8 ppm ($CF_3$, q, $^1J(^{19}F-^{13}C)$=288 Hz)—120.7 ppm (1CH)—130.0 ppm, 147.9 ppm and 149.1 ppm (3Cq)—157.5 ppm (C=O, $^2J(^{19}F-^{13}C)$=37 Hz).

Preparation B:

N-{2-[2-(chloromethyl)-4,5-dimethoxyphenyl]ethyl}-2,2,2-trifluoroacetamide

In a three-necked flask, mix N-[2-(3,4-dimethoxyphenyl)ethyl]-2,2,2-trifluoroacetamide (35 g, 126 mmoles) and 37% aqueous formaldehyde (776 mL, 1.014 mole) in 120 mL of dichloromethane at 0° C. To the resulting two-phase mixture slowly add, at 0° C., 345 mL of 37% aqueous hydrochloric acid solution and heat at 40° C. After being in contact for 3 hours, hydrolyse the mixture using 250 mL of water and wash the aqueous phase with dichloromethane (2×100 mL). Combine the organic phases, dry them over $MgSO_4$ and carry out drying in vacuo to obtain a beige meringue (38.2 g). The product obtained is recrystallised from toluene to obtain 31.5 g of a white powder corresponding to the title compound.

Yield: 77%
m.p.: 140° C.
$^1$H NMR ($CDCl_3$, 400 MHz): 2.89 ppm (2H, t)—3.58 ppm (2H, q)—3.79 ppm (3H, s)—3.81 ppm (3H,s)—4.54 ppm (2H, s)—6.45 ppm (NH)—6.60 ppm (1H, s)—6.77 ppm (1H, s).
$^{13}$C NMR ($CDCl_3$, 100 MHz): 31.0 ppm ($CH_2$)—40.8 ppm ($CH_2$)—44.4 ppm ($CH_2$)—55.9 ppm ($CH_3$)—56.0 ppm ($CH_3$)—112.7 ppm (CH)—113.6 ppm (CH)—115.8 ppm ($CF_3$, q, $^1J(^{19}F-^{13}C)$=288 Hz)—127.7 ppm, 129.1 ppm, 148.0 ppm and 150.0 ppm (4Cq)—157.6 ppm (C=O, $^2J(^{19}F-^{13}C)$=37 Hz).

Preparation C:

N-{2-[2-(cyanomethyl)-4,5-dimethoxyphenyl]ethyl}-2,2,2-trifluoroacetamide

In a three-necked flask stir, at ambient temperature, a suspension of sodium cyanide (9.8 g, 200 mmoles) in 160 mL of DMSO. Add to the suspension, dropwise, a solution of N-{2-[2-(chloromethyl)-4,5-dimethoxyphenyl]ethyl}-2,2,2-trifluoroacetamide (26 g, 798 mmoles) in 80 mL of DMSO. After being in contact for 1 hour 30 minutes at ambient temperature, hydrolyse the mixture using 300 mL of water and extract the mixture with dichloromethane (3×150 mL). Combine the organic phases and wash them with 10% aqueous solution of NaOAc (150 mL) and saturated aqueous NaCl solution (4×150 mL), then dry them over $MgSO_4$ and carry out drying in vacuo. The product obtained is recrystallised from toluene (66 mL) to obtain 12.8 g of a white powder corresponding to the title compound.

Yield: 51%
m.p.: 131° C.
$^1$H NMR (DMSO, 400 MHz): 2.78 ppm (2H, t)—3.38 ppm (2H, q)—3.73 ppm (6H, s)—3.91 ppm (2H, s)—6.80 ppm (1H, s)—6.95 ppm (1H, s)—9.52 ppm (NH, t).
$^{13}$C NMR (DMSO, 100 MHz): 19.8 ppm ($CH_2$)—31.0 ppm ($CH_2$)—39.6 ppm ($CH_2$)—55.4 ppm ($CH_3$)—55.5 ppm ($CH_3$)—113.1 ppm (CH)—113.7 ppm (CH)—115.9 ppm ($CF_3$, q, $^1J(^{19}F-^{13}C)$=288 Hz)—119.3 ppm, 121.2 ppm, 129.0 ppm, 147.5 ppm and 148.2 ppm (5Cq)—156.2 ppm (C=O, $^2J(^{19}F-^{13}C)$=36 Hz).

Preparation D:

[2-(2-aminoethyl)-4,5-dimethoxyphenyl]acetonitrile

Heat, at 50° C., a mixture of N-{2-[2-(cyanomethyl)-4,5-dimethoxyphenyl]ethyl}-2,2,2-trifluoroacetamide (20.5 g, 64.8 mmoles), ethanol (160 mL), potassium carbonate (13.2 g, 97.2 mmoles) and water (40 mL). After being in contact for 1 hour 30 minutes, extract the mixture by adding 200 mL of dichloromethane and 100 mL of saturated aqueous NaCl solution. Extract the aqueous phase with 100 mL of dichloromethane. Combine the organic phases, wash them with saturated aqueous NaCl solution (100 mL), dry them over $MgSO_4$ and carry out drying in vacuo to obtain 10 g of a yellow oil corresponding to the title compound.

Yield: 70%
m.p.: 78° C.
$^1$H NMR (DMSO, 400 MHz): 2.61 ppm (2H, m)—2.72 ppm (2H, m)—3.40 to 3.00 ($NH_2$+HDO)—3.72 ppm (3H, s)—3.73 ppm (3H, s)—3.90 ppm (2H, s)—6.81 ppm (1H, s)—6.92 ppm (1H, s)
$^{13}$C NMR (DMSO, 100 MHz): 20.0 ppm ($CH_2$)—35.9 ppm ($CH_2$)—420.9 ppm ($CH_2$)—55.5 ppm ($CH_3$)—55.6 ppm ($CH_3$)—113.0 ppm (CH)—113.7 ppm (CH)—119.6 ppm, 121.0 ppm, 131.0 ppm, 147.1 ppm and 148.3 ppm (5Cq).

Preparation E:

3-[{[(7S)-3,4-dimethoxybicyclo[4.2.0]octa-1,3,5-trien-7-yl]methyl}methyl)amino]-1-propanol Heat, at 50° C., a mixture of [(7S)-3,4-dimethoxybicyclo[4.2.0]octa-1,3,5-trien-7-yl]-N-methylmethanamine hydrochloride (20 g, 82 mmoles), triethylamine (34.2 mL, 246 mmoles) and 3-bromo-1-propanol (14.8 g, 107 mmoles) in 100 mL of THF with 5% DMF. After being in contact for 24 hours, hydrolyse the mixture using 80 mL of water and extract with 80 mL of dichloromethane. Wash the organic phase with saturated aqueous NaCl solution (5×60 mL), dry it over $MgSO_4$ and carry out drying to obtain 23.7 g of a yellow oil corresponding to the title compound.

Yield: 96%
$^1$H NMR ($CDCl_3$, 400 MHz): 1.66 ppm (2H, m)—2.31 ppm (3H, s)—2.50 to 2.70 ppm (5H, m)—3.21 ppm (1H, dd)—3.54 ppm (1H, m)—3.77 ppm (6H, s and 2H, m)—6.62 ppm (1H, s)—6.69 ppm (1H, s).
$^{13}$C NMR ($CDCl_3$, 100 MHz): 27.7 ppm ($CH_2$)—34.8 ppm ($CH_2$)—40.4 ppm (CH)—42.3 ppm ($CH_3$)—56.2 ppm ($CH_3$)—56.3 ppm ($CH_3$)—59.1 ppm ($CH_2$)—62.8 ppm ($CH_2$)—64.9 ppm ($CH_2$)—106.7 ppm (CH)—107.4 ppm (CH)—134.8 ppm, 138.5 ppm, 140.4 ppm, and 149.9 ppm (4Cq).

Preparation F:

3-chloro-N-{[(7S)-3,4-dimethoxybicyclo[4.2.0]octa-1,3,5-trien-7-yl]methyl}-N-methyl-1-propanamine To a mixture of 3-[{[(7S)-3,4-dimethoxybicyclo[4.2.0]octa-1,3,5-trien-7-yl]methyl}(methyl)-amino]-1-propanol (20.8 g, 78.4 mmoles) and triethylamine (11 mL, 78.9 mmoles) in 200 mL of dichloromethane add, at ambient temperature, 8.65 mL of thionyl chloride (157 mmoles). After being in contact for 3 hours at 40° C., hydrolyse the mixture using 150 mL of water and 30 mL of aqueous 1N NaOH solution. Adjust the pH of the aqueous phase to 10 using aqueous 10N NaOH solution and extract with 50 mL of dichloromethane. Combine the organic phases and wash them with saturated aqueous $Na_2CO_3$ solution (100 mL), dry them over $MgSO_4$ and carry out drying in vacuo to obtain 19.8 g of a brown oil corresponding to the title compound.

Yield: 89%

$^1$H NMR ($CDCl_3$, 400 MHz): 1.90 ppm (2H, m)—2.28 ppm (3H, s)—2.65 ppm (3H, m)—2.68 ppm (2H, m)—3.19 ppm (1H, dd)—3.54 ppm (1H, m)—3.56 ppm (2H, t)—3.78 ppm (6H, s)—6.62 ppm (1H, s)—6.66 ppm (1H, s).

$^{13}$C NMR ($CDCl_3$, 100 MHz): 30.2 ppm ($CH_2$)—35.0 ppm ($CH_2$)—40.6 ppm (CH)—42.6 ppm ($CH_3$)—43.1 ppm ($CH_2$)—54.8 ppm ($CH_2$)—56.2 ppm ($CH_3$)—56.3 ($CH_3$)—62.0 ppm ($CH_2$)—106.8 ppm (CH)—107.4 ppm (CH)—135.0 ppm, 135.0 ppm, 149.3 ppm and 149.9 ppm (4Cq).

Preparation G:

3-chloro-N-{[(7S)-3,4-dimethoxybicyclo[4.2.0]octa-1,3,5-trien-7-yl]methyl}-N ethyl-1-propanamine oxalate To a solution of 3-chloro-N-{[(7S)-3,4-dimethoxybicyclo[4.2.0]octa-1,3,5-trien-7-yl]methyl}-N-methyl-1-propanamine (19.8 g, 69.8 mmoles) in 60 mL of ethyl acetate heated at reflux there is added a solution of oxalic acid (6.91 g, 76.7 mmoles) in 60 mL of ethanol. Precipitation from the mixture occurs during contact at reflux. After returning to ambient temperature, the mixture is filtered and washed with 20 mL of ethanol to obtain 17.35 g of a brown powder corresponding to the title compound.

Yield: 67% m.p.: 154° C.

$^1$H NMR (DMSO, 400 MHz): 2.14 ppm (2H, m)—2.75 ppm (3H, s)—2.88 ppm (1H, dd)—3.12 ppm (2H, m)—3.16 ppm (1H, dd)—3.28 ppm (1H, dd)—3.41 ppm (1H, dd)—3.69 to 3.75 ppm (9H, m)—6.79 ppm (1H, s)—6.86 ppm (1H, s)—9.21 ppm (20H).

$^{13}$C NMR (DMSO, 100 MHz): 26.8 ppm ($CH_2$)—35.0 ppm ($CH_2$)—37.5 ppm (CH)—40.1 ppm ($CH_2$)—42.6 ppm ($CH_2$)—53.1 ppm ($CH_2$)—55.8 ppm ($CH_3$)—55.9 ppm ($CH_3$)—58.6 ppm ($CH_2$)—107.6 ppm (CH)—108.0 ppm (CH)—134.2 ppm, 135.7 ppm, 149.3 ppm and 150.2 ppm (4Cq)—164.4 ppm (C=O).

Preparation H:

Ethyl N-{2-[2-(cyanomethyl)-4,5-dimethoxyphenyl]ethyl}-β-alaninate oxalate

A mixture of [2-(2-aminoethyl)-4,5-dimethoxyphenyl]acetonitrile (6.5 g, 29.5 mmol) and ethyl acrylate (3.9 ml, 36 mmol, 1.2 eq.) in 120 mL of ethanol is stirred for 20 hours at ambient temperature. The reaction mixture is subjected to drying in vacuo; then the crude reaction mixture is taken up in a mixture of ethyl acetate (133 mL) and ethanol (13 mL) and is heated at reflux in the presence of oxalic acid (2.52 g, 28 mmol, 0.95 eq.). Precipitation from the mixture occurs during contact at reflux. After returning to ambient temperature, the mixture is filtered and washed with 19 ml of ethyl acetate to obtain a white powder (9 g) corresponding to the title compound.

Yield: 74% m.p.: 218° C.

$^1$H NMR ($CDCl_3$, 400 MHz): 1.19 ppm (3H, t)—2.74 ppm (2H, t)—2.88 ppm (2H, m)—3.06 ppm (2H, m)—3.17 ppm (2H, t)—3.74 ppm (3H, s)—3.75 ppm (3H, s)—3.93 ppm (2H, s)—4.09 ppm (2H, quadruplet)—6.88 ppm (1H, s)—6.97 ppm (1H, s).

$^{13}$C NMR ($CDCl_3$, 100 MHz): 14.00 ppm ($CH_3$)—19.86 ppm ($CH_2$)—28.28 ppm ($CH_2$)—30.39 ppm ($CH_2$)—42.25 ppm ($CH_2$)—47.19 ppm ($CH_2$)—55.60 ppm ($CH_3$)—55.62 ppm ($CH_3$)—60.53 ppm ($CH_2$)—113.13 ppm (CH)—113.74 ppm (CH)—119.36 ppm (Cq)—121.40 ppm (Cq)—127.70 ppm (Cq)—147.73 ppm (Cq)—148.42 ppm (Cq)—164.65 ppm (Cq)—170.29 ppm (Cq).

Preparation I:

(2-{2-[(3-hydroxypropyl)amino]ethyl}-4,5-dimethoxyphenyl)acetonitrile

To a suspension of 10.8 g of $NaBH_4$ (284 mmol, 11 eq.) in 110 mL of THF there is added, at several points over a period of time, ethyl N-{2-[2-(cyanomethyl)-4,5-dimethoxyphenyl]ethyl}-β-alaninate oxalate (10.6 g, 25.9 mmol). Stirring is carried out for 30 minutes at ambient temperature, and then 23.1 ml of methanol (570 mmol, 22 eq.) are poured in dropwise. The mixture is heated for 16 hours at 60° C., and is then hydrolysed using 100 mL of 5N hydrochloric acid. There are then added 100 mL of dichloromethane and 200 mL of demineralised water. After separation of the phases, 50 ml of 10N sodium hydroxide solution are added (pH>10) to the aqueous phase and extraction is carried out using 3×70 mL of dichloromethane. The organic phases are combined and washed with 2×75 mL of saturated aqueous NaCl solution and then dried over $MgSO_4$. After carrying out drying in vacuo, there are obtained 6.15 g of a colourless oil corresponding to the title compound.

Yield: 85%

$^1$H NMR ($CDCl_3$, 400 MHz): 1.54 ppm (2H, quintuplet)—2.59 ppm (2H, t)—2.66 ppm (4H, m)—3.44 ppm (2H, t)—3.72 ppm (3H, s)—3.73 ppm (3H, s)—3.88 ppm (2H, s)—6.82 ppm (1H, s)—6.91 ppm (1H, s).

$^{13}$C NMR ($CDCl_3$, 100 MHz): 19.96 ppm ($CH_2$)—32.44 ppm ($CH_2$)—32.69 ppm ($CH_2$)—46.73 ppm ($CH_2$)—50.58 ppm ($CH_2$)—55.51 ppm ($CH_3$)—55.59 ppm ($CH_3$)—59.62 ppm ($CH_2$)—112.98 ppm (CH)—113.65 ppm (CH)—119.54 ppm (Cq)—120.92 ppm (Cq)—131.27 ppm (Cq)—147.03 ppm (Cq)—148.23 ppm (Cq).

Preparation J:

(2-{2-[(3-chloropropyl)amino]ethyl}-4,5-dimethoxyphenyl)acetonitrile

To a mixture of 2-{2-[(3-hydroxypropyl)amino]ethyl}-4,5-dimethoxyphenyl)acetonitrile (1.7 g, 6.1 mmol) and triethylamine (2.5 ml, 18.3 mmol, 3 eq.) in 16 mL of dichloromethane there is added, by pouring dropwise, a solution composed of 885 μL of thionyl chloride (12.2 mmol, 2 eq.) and 1 mL of dichloromethane. The mixture is heated for 2 hours at 40° C., and then, once it has returned to ambient temperature, is hydrolysed using 15 mL of demineralised water. After stirring overnight at ambient temperature, 3 mL of aqueous 10N sodium hydroxide solution (pH>10) are added. After separation of the phases, the organic phase is removed and kept. The aqueous phase is extracted with 20 ml of dichloromethane. The organic phases are combined and washed with 25 mL of saturated aqueous NaCl solution and then dried over MgSO₄. After carrying out drying in vacuo, 1.5 g of a brown oil corresponding to the title compound are obtained.

Yield: 83%

$^1$H NMR (CDCl$_3$, 400 MHz): 1.91 ppm (2H, quintuplet)—2.75 ppm (2H, m)—2.77 ppm (2H, m)—2.83 ppm (2H, m)—3.59 ppm (2H, t)—3.71 ppm (2H, s)—3.86 ppm (3H, $)—3.87 ppm (3H, s)—6.71 ppm (1H, s)—6.84 ppm (1H, s).

$^{13}$C NMR (CDCl$_3$, 100 MHz): 21.11 ppm (CH$_2$)—32.73 ppm (CH$_2$)—33.16 ppm (CH$_2$)—43.04 ppm (CH$_2$)—46.88 ppm (CH$_2$)—50.45 ppm (CH$_2$)—56.03 ppm (CH$_3$)—56.08 ppm (CH$_3$)—112.17 ppm (CH)—113.08 ppm (CH)—118.20 ppm (CH)—120.02 ppm (Cq)—130.19 ppm (Cq)—147.72 ppm (Cq)—148.74 ppm (Cq).

EXAMPLE 1

{2-[2-({3-[{[(7S)-3,4-dimethoxybicyclo[4.2.0]octa-1,3,5-trien-7-yl]methyl}(methyl)-amino]propyl}amino)ethyl]-4,5-dimethoxyphenyl}acetonitrile First Variant A mixture of 3-chloro-N-{[(7S)-3,4-dimethoxybicyclo [4.2.0]octa-1,3,5-trien-7-yl]methyl}-N-methyl-1-propanamine oxalate (15 g, 40.1 mmoles) and 85 mL of aqueous 1N NaOH solution in 150 mL of dichloromethane is stirred for 1 hour at ambient temperature. The mixture is separated, and the organic phase is dried over MgSO₄ and subjected to drying in vacuo to obtain 11.3 g of an orange oil corresponding to 3-chloro-N-{[(7S)-3,4-dimethoxybicyclo-[4.2.0]octa-1,3,5-trien-7-yl]methyl}-N-methyl-1-propanamine.

The product obtained above is stirred at ambient temperature in the presence of potassium iodide (1.46 g, 8.78 mmoles) in 200 mL of acetonitrile. To the resulting mixture there are added, in succession, triethylamine (5.6 mL, 40.2 mmoles) and then [2-(2-aminoethyl)-4,5-dimethoxyphenyl] acetonitrile (8.82 g, 40.1 mmoles) dissolved in 50 mL of acetonitrile. After being in contact for 24 hours at 60° C., 150 mL of water are added and the mixture is extracted by adding dichloromethane (150 mL). The organic phase is washed with 185 mL of water and 15 mL of 37% aqueous hydrochloric acid solution. The aqueous phase is collected, 185 mL of saturated aqueous NaHCO₃ solution are added and the resulting phase is extracted with 150 mL of dichloromethane. The organic phase is dried over MgSO₄ and subjected to drying to obtain 14.1 g of an orange oil corresponding to the title compound.

Yield: 75%

Second Variant

A mixture of (2-{2-[(3-chloropropyl)amino]ethyl}-4,5-dimethoxyphenyl)acetonitrile (870 mg, 2.93 mmol), 1-[(7S)-3,4-dimethoxybicyclo[4.2.0]octa-1,3,5-trien-7-yl]-N-methyl-methanamine hydrochloride (714 mg, 2.93 mmol) and triethylamine (1.25 ml, 8.97 mmol, 3 eq.) in 10 mL of acetonitrile is heated at reflux for 6 hours. After returning to ambient temperature, the mixture is filtered in vacuo. The filtrate is dried over MgSO₄ and subjected to drying in vacuo to obtain a brown meringue (0.9 g, 66%) corresponding to the title compound.

Yield: 66%

$^1$H NMR (CDCl$_3$, 400 MHz): 2.10 ppm (12H, s)—2.45 ppm (2H, m)—2.84 to 2.94 ppm (2H, m)—3.10 to 3.60 ppm (10H, m) 3.80 ppm (6H, m)—4.36 ppm (NH, s)—6.56 ppm (1H, s)—6.69 ppm (1H, s)—6.78 ppm (1H, s)—6.83 ppm (1H, s).

$^{13}$C NMR (CDCl$_3$, 100 MHz): 21.3 ppm (CH$_2$)—21.8 ppm (CH$_2$)—29.0 ppm (CH$_2$)—36.2 ppm (CH$_2$)—37.5 ppm (CH)—40.7 ppm (CH$_3$)—45.6 ppm (CH$_2$)—48.6 ppm (CH$_2$)—55.1 ppm (CH$_2$)—56.1 ppm (CH$_3$)—56.2 ppm (CH$_3$)—56.4 ppm (CH$_3$)—56.6 ppm (CH$_3$)—60.1 ppm (CH$_2$)—107.1 ppm (CH)—107.3 ppm (CH)—112.7 ppm (CH)—113.6 ppm (CH)—119.0 ppm, 120.8 ppm, 126.7 ppm, 134.1 ppm, 134.2 ppm, 148.5 ppm, 149.2 ppm, 149.9 ppm and 150.9 ppm (9C q).

EXAMPLE 2

{2-[2-({3-[{[(7S)-3,4-dimethoxybicyclo[4.2.0]octa-4,3,5-trien-7-yl]methyl}(methyl)-amino]propyl}amino)ethyl]-4,5-dimethoxyphenyl}acetic acid 1.3 g of the product obtained in Example 1 (2.77 mmoles) and 1.11 g of NaOH pellets (27.7 mmoles) are heated at reflux in 6.2 mL of ethanol and 14.6 mL of water. After refluxing for 6 hours, the reaction mixture is hydrolysed using 10 mL of water, and 20 mL of dichloromethane are added. The organic phase is extracted with 20 mL of water. The aqueous phases are combined and washed with 15 mL of dichloromethane. The pH of the washed aqueous phase is adjusted to 7 using aqueous 37% hydrochloric acid solution and then drying in vacuo is carried out. The yellow solid thereby obtained is taken up in 40 mL of acetone at ambient temperature. The suspension obtained is filtered in vacuo. The filtration liquors are subjected to drying in vacuo to obtain 0.7 g of a yellow meringue corresponding to the title compound.

Yield: 52%

$^1$H NMR (CDCl$_3$, 400 MHz): 2.10 ppm (2H, m)—2.54 ppm (3H, s)—2.70 to 3.30 ppm (12H, m)—3.47 ppm (2H, s)—3.55 ppm (1H, m)—3.71 ppm (3H, s)—3.73 ppm (3H, s)—3.74 ppm (3H, s)—3.75 ppm (3H, s)—6.55 ppm (H, s)—6.62 ppm (H, s)—6.63 ppm (H, s)—6.64 ppm (H, s).

$^{13}$C NMR (CDCl$_3$, 100 MHz): 20.7 ppm (CH$_2$)—28.1 ppm (CH$_2$)—34.9 ppm (CH$_2$)—37.0 ppm (CH)—39.1 ppm (CH$_3$)—40.1 ppm (CH$_2$)—44.7 ppm (CH$_2$)—48.1 ppm (CH$_2$)—52.9 ppm (CH$_2$)—54.8 ppm (CH$_3$)—54.9 ppm (CH$_3$)—55.2 ppm (CH$_3$)—55.3 ppm (CH$_3$)—59.1 ppm (CH$_2$)—105.8 ppm (CH)—106.2 ppm (CH)—111.6 ppm (CH)—112.6 ppm (CH)—126.3 ppm, 127.0 ppm, 133.2 ppm, 134.2 ppm, 146.9 ppm, 147.2 ppm, 148.7 ppm, and 149.6 ppm (8C q)—176.9 ppm (C=O).

EXAMPLE 3

3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one In a three-necked flask, mix 0.7 g of the product obtained in Example 2 (1.44 mmoles) and 0.4 mL of triethylamine (2.88 mmoles) in 14 mL of dichloromethane. Ice the mixture at 5° C. and add, dropwise, 0.16 mL of thionyl chloride (2.16 mmoles). Stir for 1 hour at 30° C. and then hydrolyse the mixture using 12 mL of aqueous 1N NaOH solution. Wash the organic phase with, in succession, 10 mL of water and then 10 mL of saturated aqueous NaCl solution. Dry the organic phase over MgSO₄ and carry out drying in vacuo to obtain 0.5 g of an orange oil corresponding to the title compound.

Yield: 74%

$^1$H NMR (CDCl$_3$, 400 MHz): 1.78 ppm (2H, m)—2.32 ppm (3H, s)—2.40 to 2.80 ppm (5H, m)—3.16 ppm (2H, t)—3.19 ppm (1H, m)—3.42 ppm (3H, m)—3.55 to 3.80 ppm (16H, m)—6.50 ppm (1H, s)—6.52 ppm (1H, s)—6.61 ppm (1H, s)—6.65 ppm (1H, s).

$^{13}$C NMR (CDCl$_3$, 100 MHz): 25.0 ppm (CH$_2$)—31.3 ppm (CH$_2$)—34.3 ppm (CH$_2$)—39.2 ppm (CH)—41.2 ppm (CH$_3$)—41.6 ppm (CH$_2$)—43.9 ppm (CH$_2$)—45.6 ppm (CH$_2$)—54.1 ppm (CH$_2$)—54.9 ppm (CH$_3$)—54.9 ppm (CH$_3$)—55.2 ppm (CH$_3$)—55.3 ppm (CH$_3$)—60.7 ppm (CH$_2$)—105.8 ppm (CH)—106.4 ppm (CH)—112.1 ppm (CH)—112.9 ppm (CH)—122.4 ppm, 126.4 ppm, 126.4 ppm, 133.8 ppm, 146.1 ppm, 146.8 ppm, 148.4 ppm and 148.9 ppm (8C q)—171.2 ppm (C=O).

The invention claimed is:

1. A process for the synthesis of ivabradine of formula (I):

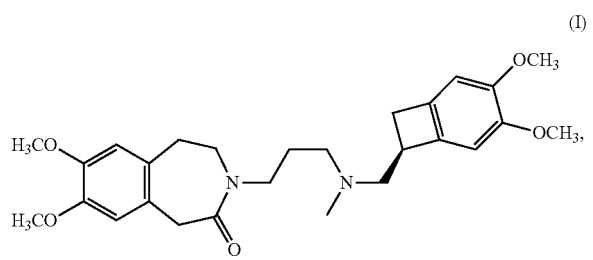 [SMILES: COc1cc2c(cc1OC)CC(=O)N(CCCN(C)C[C@H]1Cc3cc(OC)c(OC)cc31)CC2]

(I)

wherein a compound of formula (VI):

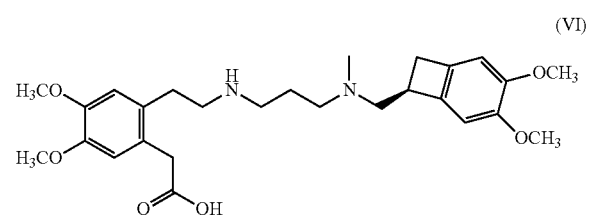 [SMILES: COc1cc(CCNCCCN(C)C[C@H]2Cc3cc(OC)c(OC)cc32)c(CC(=O)O)cc1OC]

(VI)

is subjected to a lactamisation reaction,
in the presence of a coupling agent and a base,
in an organic solvent,
to yield ivabradine of formula (I), which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

2. The process according to claim 1, wherein the coupling agent used to carry out the reaction for lactamisation of the compound of formula (VI) is selected from oxalyl chloride, thionyl chloride, N,N-dicyclohexylcarbodiimide (DCC), 1-ethyl-3-(3-dimethylaminopropyl)carbodiimide (EDCI), N,N-carbonyldiimidazole (CDI), 1-propanephosphonic acid cyclic anhydride (T3P) and 1-(methylsulphonyl)-1H-benzotriazole.

3. The process according to claim 2, wherein the coupling agent used to carry out the reaction for lactamisation of the compound of formula (VI) is thionyl chloride.

4. The process according to claim 3, wherein the amount of thionyl chloride used to carry out the reaction for lactamisation of the compound of formula (VI) is between 1 and 5 equivalents.

5. The process according to claim 1, wherein the base used to carry out the reaction for lactamisation of the compound of formula (VI) is selected from triethylamine, diisopropylethylamine and pyridine.

6. The process according to claim 5, wherein the base used to carry out the reaction for lactamisation of the compound of formula (VI) is triethylamine.

7. The process according to claim 1, wherein the organic solvent used to carry out the reaction for lactamisation of the compound of formula (VI) is selected from dichloromethane, tetrahydrofuran, acetonitrile, acetone and toluene.

8. The process according to claim 7, wherein the organic solvent used to carry out the reaction for lactamisation of the compound of formula (VI) is dichloromethane.

9. The process according to claim 1, wherein the reaction for lactamisation of the compound of formula (VI) is carried out at a temperature between 0° C. and 40° C.

10. The process according to claim 1, wherein the compound of formula (VI) is prepared starting from the compound of formula (VII):

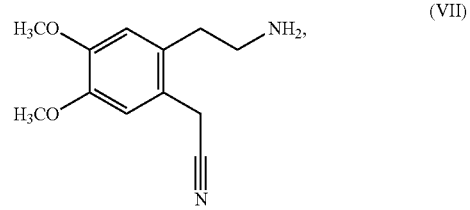 [SMILES: COc1cc(CC#N)c(CCN)cc1OC]

(VII)

which is reacted with a compound of formula (VIII):

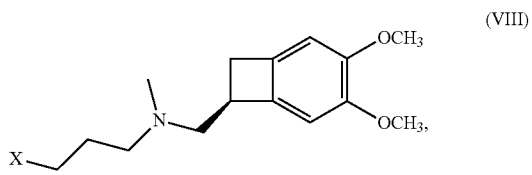

(VIII)

wherein X represents a halogen atom, a mesylate group or a tosylate group,
in the presence of a base,
in an organic solvent,
to yield a compound of formula (IX):

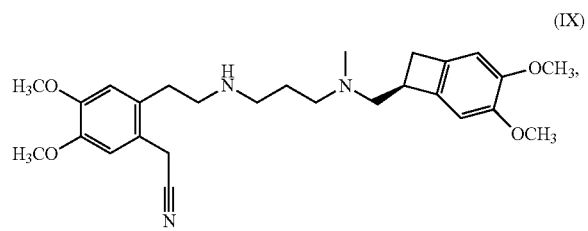 [SMILES: COc1cc(CC#N)c(CCNCCCN(C)C[C@H]2Cc3cc(OC)c(OC)cc32)cc1OC]

(IX)

which is hydrolysed, by the action of a base in a mixture of organic solvent and water, to form the compound of formula (VI):

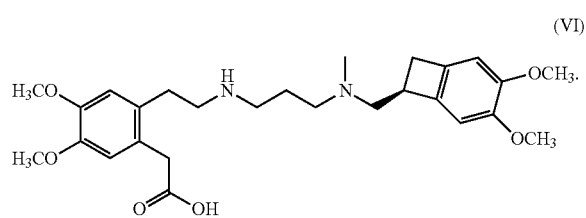

11. The process according to claim 1, wherein the compound of formula (VI) is prepared starting from a compound of formula (X):

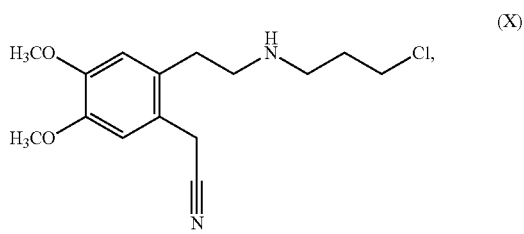 [SMILES: COc1cc(CC#N)c(CCNCCCCl)cc1OC]

which is reacted with the hydrochloride of a compound of formula (III):

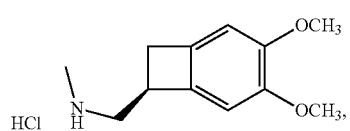

in the presence of a base,
in an organic solvent,
to yield a compound of formula (IX):

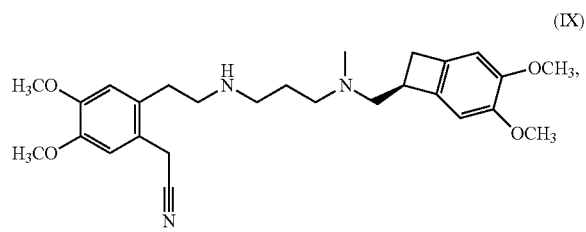 [SMILES: COc1cc(CC#N)c(CCNCCCN(C)C[C@H]2Cc3cc(OC)c(OC)cc32)cc1OC]

which is hydrolysed, by the action of a base in a mixture of organic solvent and water, to form the compound of formula (VI):

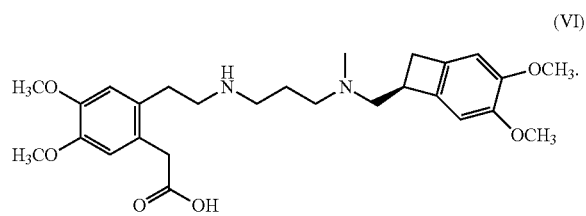 [SMILES: COc1cc(CCNCCCN(C)C[C@H]2Cc3cc(OC)c(OC)cc32)c(CC(=O)O)cc1OC]

12. The process according to claim 10, wherein the base used to carry out the alkylation reaction between the compound of formula (VII) and the compound of formula (VIII) is selected from potassium carbonate, sodium carbonate, caesium carbonate, potassium hydrogen carbonate, sodium hydrogen carbonate, triethylamine, diisopropylethylamine and pyridine.

13. The process according to claim 12, wherein the base used to carry out the alkylation reaction between the compound of formula (VII) and the compound of formula (VIII) is triethylamine.

14. The process according to claim 10, wherein the organic solvent used to carry out the alkylation reaction between the compound of formula (VII) and the compound of formula (VIII) is selected from acetonitrile, acetone, methyl ethyl ketone (MEK), dimethylformamide (DMF), N-methylpyrrolidone (NMP) and dimethyl sulphoxide (DMSO).

15. The process according to claim 14, wherein the organic solvent used to carry out the alkylation reaction between the compound of formula (VII) and the compound of formula (VIII) is acetonitrile.

16. The process according to claim 10, wherein the alkylation reaction between the compound of formula (VII) and the compound of formula (VIII) is carried out at a temperature between 20° C. and 100° C.

17. The process according to claim 10, wherein the base used to carry out the hydrolysis of the compound of formula (IX) to form the compound of formula (VI) is selected from potassium hydroxide, sodium hydroxide, lithium hydroxide and barium hydroxide.

18. The process according to claim 17, wherein the base used to carry out the hydrolysis of the compound of formula (IX) to form the compound of formula (VI) is sodium hydroxide.

19. The process according to claim 10, wherein the organic solvent used to carry out the hydrolysis of the compound of formula (IX) to form the compound of formula (VI) is an alcoholic solvent.

20. The process according to claim 19, wherein the alcoholic solvent used to carry out the hydrolysis of the compound of formula (IX) to form the compound of formula (VI) is selected from methanol, ethanol, isopropanol and butanol.

21. The process according to claim 20, wherein the alcoholic solvent used to carry out the hydrolysis of the compound of formula (IX) to form the compound of formula (VI) is ethanol.

22. The process according to claim 10, wherein the hydrolysis of the compound of formula (IX) to form the compound of formula (VI) is carried out at a temperature between 0° C. and 110° C.

23. The process according to claim 11, wherein the based used to carry out the alkylation reaction between the compound of formula (X) and the hydrochloride of the compound of formula (III) is selected from potassium carbonate, sodium carbonate, caesium carbonate, potassium hydrogen carbonate, sodium hydrogen carbonate, triethylamine, diisopropylethylamine and pyridine.

24. The process according to claim 23, wherein the based used to carry out the alkylation reaction between the compound of formula (X) and the hydrochloride of the compound of formula (III) is triethylamine.

25. The process according to claim 11, wherein the organic solvent used to carry out the alkylation reaction between the compound of formula (X) and the hydrochloride of the compound of formula (III) is selected from acetonitrile, acetone, methyl ethyl ketone (MEK), dimethylformamide (DMF), N-methylpyrrolidone (NMP) and dimethyl sulphoxide (DMSO).

26. The process according to claim 25, wherein the organic solvent used to carry out the alkylation reaction between the compound of formula (X) and the hydrochloride of the compound of formula (III) is acetonitrile.

27. The process according to claim 11, wherein the alkylation reaction between the compound of formula (X) and the hydrochloride of the compound of formula (III) is carried out at a temperature between 20° C. and 100° C.

28. The process according to claim 11, wherein the base used to carry out the hydrolysis of the compound of formula (IX) to form the compound of formula (VI) is selected from potassium hydroxide, sodium hydroxide, lithium hydroxide and barium hydroxide.

29. The process according to claim 28, wherein the base used to carry out the hydrolysis of the compound of formula (IX) to form the compound of formula (VI) is sodium hydroxide.

30. The process according to claim 11, wherein the organic solvent used to carry out the hydrolysis of the compound of formula (IX) to form the compound of formula (VI) is an alcoholic solvent.

31. The process according to claim 30, wherein the alcoholic solvent used to carry out the hydrolysis of the compound of formula (IX) to form the compound of formula (VI) is selected from methanol, ethanol, isopropanol and butanol.

32. The process according to claim 31, wherein the alcoholic solvent used to carry out the hydrolysis of the compound of formula (IX) to form the compound of formula (VI) is ethanol.

33. The process according to claim 11, wherein the hydrolysis of the compound of formula (IX) to form the compound of formula (VI) is carried out at a temperature between 0° C. and 110° C.

34. A compound of formula (VI):

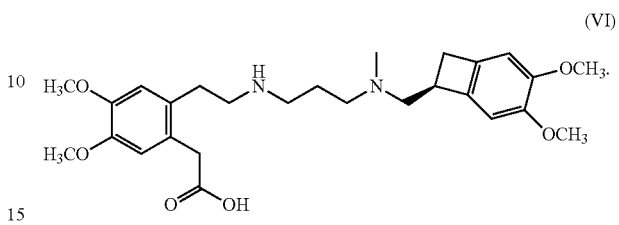

(VI)

35. A compound of formula (IX):

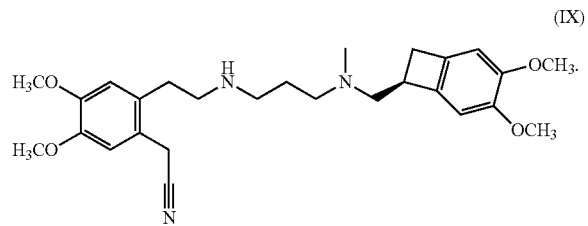 [SMILES: COc1cc(CC#N)c(CCNCCCN(C)C[C@H]2Cc3cc(OC)c(OC)cc32)cc1OC]

(IX)

* * * * *